United States Patent
Chen et al.

(10) Patent No.: US 9,937,491 B2
(45) Date of Patent: Apr. 10, 2018

(54) METHOD FOR PREPARING CHIRAL FERROCENE DIPHOSPHINE LIGAND

(71) Applicant: HENAN ACADEMY OF SCIENCES CHEMICAL RESEARCH INSTITUTE CO. LTD., Zhengzhou (CN)

(72) Inventors: Hui Chen, Zhengzhou (CN); Zhenqiang Yang, Zhengzhou (CN); Yinlong Zhang, Zhengzhou (CN); Shunwei Zhao, Zhengzhou (CN); Duo Zhou, Zhenghou (CN); Ruina Yang, Zhengzhou (CN); Minqing Sun, Zhengzhou (CN); Zheng Duan, Zhengzhou (CN)

(73) Assignee: HENAN ACADEMY OF SCIENCES CHEMICAL RESEARCH INSTITUTE CO. LTD., Zhengzhou (CN)

( * ) Notice: Subject to any disclaimer, the term of this patent is extended or adjusted under 35 U.S.C. 154(b) by 0 days.

(21) Appl. No.: 15/667,646

(22) Filed: Aug. 3, 2017

(65) Prior Publication Data
US 2017/0326537 A1    Nov. 16, 2017

Related U.S. Application Data

(63) Continuation-in-part of application No. PCT/CN2016/112288, filed on Dec. 27, 2016.

(30) Foreign Application Priority Data

Apr. 13, 2016  (CN) .......................... 2016 1 0228279

(51) Int. Cl.
| | | |
|---|---|---|
| *B01J 31/22* | (2006.01) | |
| *C08F 4/6192* | (2006.01) | |
| *B01J 31/02* | (2006.01) | |
| *C07F 15/02* | (2006.01) | |
| *C07F 9/12* | (2006.01) | |
| *G01R 33/46* | (2006.01) | |

(52) U.S. Cl.
CPC ....... *B01J 31/2295* (2013.01); *B01J 31/0258* (2013.01); *C08F 4/61922* (2013.01); *C07F 9/12* (2013.01); *C07F 15/02* (2013.01); *G01R 33/46* (2013.01)

(58) Field of Classification Search
CPC ............... B01J 31/2295; B01J 31/0258; C08F 4/61922; C07F 9/12; C07F 15/02; G01R 33/46
USPC .......................................................... 558/177
See application file for complete search history.

(56) References Cited

U.S. PATENT DOCUMENTS 7,671,225 B2 *  3/2010  Lotz et al. .............. C07F 19/00
                                                            566/28

\* cited by examiner

*Primary Examiner* — Kristin A Vajda
(74) *Attorney, Agent, or Firm* — Matthias Scholl P.C.; Matthias Scholl

(57) ABSTRACT

A method for synthesizing (R)-(−)-1-((S)-2-diphosphino ferrocene)-ethyl-diphosphine by: 1) adding vinylferrocene, a chiral catalyst, and toluene to a first drying reactor; adding a phosphorus-hydrogen compound to the first drying reactor and allowing reactants in the first drying reactor to react; cooling the first drying reactor; adding water dropwise to the first drying reactor; extracting, drying, and recrystallizing a product to yield (R)-1-ferrocenylethyl-diphosphine; 2) adding the (R)-1-ferrocenylethyl-diphosphine and ether to a second drying reactor; adding a hexane solution including diethylzinc to the second drying reactor and allowing reactants in the second drying reactor to react; adding a phosphorus-chlorine compound dropwise to the second drying reactor, and heating and refluxing the reaction mixture in the second drying reactor; adding water to quench the reaction mixture in the second drying reactor; and extracting, drying, and recrystallizing the reaction mixture.

3 Claims, No Drawings

METHOD FOR PREPARING CHIRAL FERROCENE DIPHOSPHINE LIGAND

CROSS-REFERENCE TO RELATED APPLICATIONS

This application is a continuation-in-part of International Patent Application No. PCT/CN2016/112288 with an international filing date of Dec. 27, 2016, designating the United States, now pending, and further claims foreign priority benefits to Chinese Patent Application No. 201610228279.8 filed Apr. 13, 2016. The contents of all of the aforementioned applications, including any intervening amendments thereto, are incorporated herein by reference. Inquiries from the public to applicants or assignees concerning this document or the related applications should be directed to: Matthias Scholl P.C., Attn.: Dr. Matthias Scholl Esq., 245 First Street, 18th Floor, and Cambridge, Mass. 02142.

BACKGROUND OF THE INVENTION

Field of the Invention

The invention relates to a method for synthesizing a chiral ferrocene diphosphine ligand.

Description of the Related Art

Conventionally, the preparation of the chiral ferrocene diphosphine ligands utilizes chiral N,N-dimethyl-1-ferrocenylethyl-amine (Ugi's amine) as the starting material. The synthesis of the Ugi's amine includes an acetylation step, a reduction step by using sodium dihydrobismethoxy-ethoxy-aluminate (red-aluminum), an esterification step, an aminolysis step, and a chemical resolution step. The method involves complex recrystallization process, has long reaction route, and is not suitable for industrial production.

SUMMARY OF THE INVENTION

In view of the above-described problems, it is one objective of the invention to provide a method for synthesizing a chiral ferrocene diphosphine ligand that features relatively short synthesis route and simple operation, thus being suitable for industrial production.

To achieve the above objective, in accordance with one embodiment of the invention, there is provided a method for synthesizing a chiral ferrocene diphosphine ligand. A reaction route of the method is as follows:

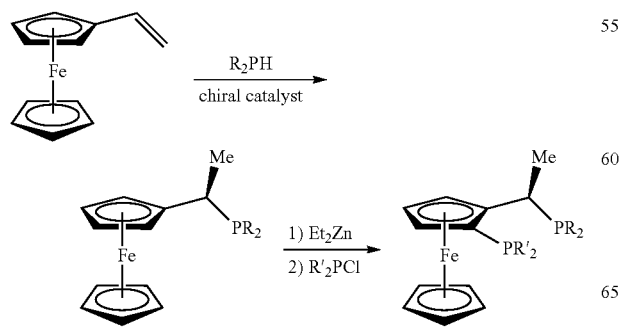

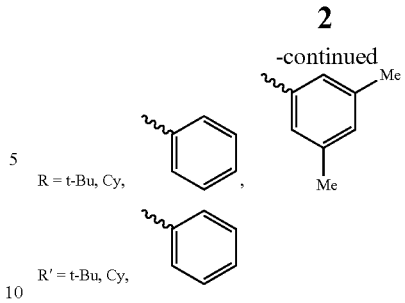

R = t-Bu, Cy,

R' = t-Bu, Cy,

The method comprises:
1) adding vinylferrocene, a chiral catalyst, and toluene as a solvent to a first drying reactor under inert gas protection; adding a phosphorus-hydrogen compound to the first drying reactor and allowing reactants in the first drying reactor to react for between 10 and 12 hrs at a temperature of between 60 and 100° C.; cooling the first drying reactor; adding water dropwise to the first drying reactor; extracting, drying, and recrystallizing a product to yield (R)-1-ferrocenylethyl-diphosphine; and
2) adding the (R)-1-ferrocenylethyl-diphosphine and ether as a solvent to a second drying reactor under inert gas protection; adding a hexane solution comprising diethylzinc to the second drying reactor and allowing reactants in the second drying reactor to react for between 1 and 3 hr(s) at a temperature of between 0 and 30° C.; adding a phosphorus-chlorine compound dropwise to the second drying reactor, and heating and refluxing the second drying reactor for between 2 to 3 hrs; adding water to quench a reaction mixture in the second drying reactor; and extracting, drying, and recrystallizing the reaction mixture to yield (R)-(–)-1-(S)-2-diphosphino ferrocene)-ethyl-diphosphine.

In a class of this embodiment, the phosphorus-hydrogen compound is di-tert-butylphosphine, dicyclohexylphosphine, diphenylphosphine, or bis(3,5-dimethylphenyl)-phosphine.

In a class of this embodiment, the phosphorus-chlorine compound is di-tert-butylchlorophosphine, dicyclohexylchlorophosphine, or diphenylchlorophosphine.

In a class of this embodiment, the chiral catalyst is (R)-3,3'-bis(3,5-dimethylphenyl)-1,1'-binaphthyl-2,2'-diyl-hydrogenphosphate, and a structural formula of the chiral catalyst is:

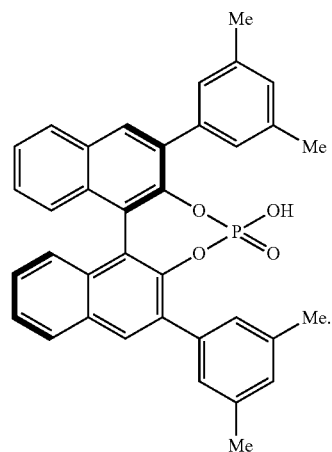

In a class of this embodiment, a molar ratio of the vinylferrocene to the chiral catalyst to the phosphorus-hydrogen compound is 1:0.01-0.1:1-1.5.

In a class of this embodiment, a molar ratio of the (R)-1-ferrocenylethyl-diphosphine to the diethylzinc is 1:1-1.5. A molar ratio of the diethylzinc to the phosphorus-chlorine compound is 1:1-1.3.

Advantages of the method for synthesizing a chiral ferrocene diphosphine ligand according to embodiments of the invention are summarized as follows:

1. The method uses vinylferrocene as the raw material, and (R)-3,3'-bis(3,5-dimethylphenyl)-1,1'-binaphthyl-2,2'-diyl hydrogenphosphate as the chiral catalyst, and the vinylferrocene reacts with phosphorus-hydrogen compound in accordance with the Markovnikov's rule, thus solving the problems of long reaction route and complex chiral separation in the prior art.

2. Due to the weak coordination ability of the diethylzinc and the phosphine, the active hydrogen on the ferrocene is selectively activated, and optical purity of the target product is effectively ensured. The enantiomeric excess (e. e.) % of the (R)-(−)-1-((S)-2-diphosphino ferrocene)-ethyl-diphosphine is higher than 99%. The method features relatively short synthesis route and simple operation. The total yield of the target product is more than 95%, thus the method is suitable for industrial production. The chiral ferrocene diphosphine compound prepared using the method can be used as the ligand of metal catalysts, and be applied to the medicinal synthesis field, etc.

DETAILED DESCRIPTION OF THE EMBODIMENTS

For further illustrating the invention, experiments detailing a method for preparing chiral ferrocene diphosphine ligand are described below.

EXAMPLE 1

(1) Synthesis of (R)-1-ferrocenylethyl-di-tert-butylphosphine

Under argon atmosphere, vinylferrocene (1 mol, 212 g), (R)-3,3'-bis(3,5-dimethylphenyl)-1,1'-binaphthyl-2,2'-diyl hydrogenphosphate (0.01 mol, 5.6 g), and 1 L of toluene were added to a first drying reactor in that order. Di-tert-butylphosphine (1 mol, 147 g) was added to the first drying reactor, and allow to react for 12 hrs at 60° C. The first drying reactor was cooled. Water was added dropwise to the first drying reactor. Liquid separation was performed, and the organic layer was dried over anhydrous magnesium sulfate, then filtrated, and distilled at reduced pressure to remove solvent and yield yellow solid. The yellow solid was recrystallized in dichloromethane and methyl alcohol to yield 347 g of (R)-1-ferrocenylethyl-di-tert-butylphosphine, and the yield was 97%. The enantiomeric excess (e. e.) % was 99.5%. $^{31}$P NMR (400 MHz, CDCl$_3$), δ: 48.7; $^1$H NMR (400 MHz, CDCl$_3$), δ: 4.35-4.14 (m, 4H, Fc-H), 3.98(m, 5H, Fc-H), 3.44 (m, 1H), 1.83(dd, J=7.2 Hz, J=3.0 Hz, 3H), 1.13(d, J=10.2 Hz, 9H), 0.98 (d, J=10.2 Hz, 9H); HRMS: Calcd for C$_{20}$H$_{31}$FeP 358.1513, Found 358.1511; measured value (calculated value) of element analysis/%: C 67.02 (67.05), H 8.70 (8.72).

(2) Synthesis of (R)-(−)-1-((S)-2-diphosphino ferrocene)-ethyl-di-tert-butylphosphine Under argon atmosphere, (R)-1-ferrocenylethyl-di-tert-butylphosphine (0.9 mol, 321 g), and 1 L of ether were added to a second drying reactor. 1 mol/L of hexane solution (0.9 mol, 0.9 L) containing diethylzinc was added to the second drying reactor and allow to react for 3 hrs at 0° C. Diphenylchlorophosphine (0.9 mol, 199 g) was added dropwise to reaction mixture, and the reaction mixture was heated and refluxed for 2 hrs. Water was added to quench the reaction mixture. Liquid separation of the reaction mixture was performed, and the organic layer was dried over anhydrous magnesium sulfate, then filtrated, and distilled at reduced pressure to remove solvent and yield yellow solid. The yellow solid was recrystallized in dichloromethane and methyl alcohol to yield 468 g of (R)-(−)-1-((S)-2-diphosphino ferrocene)-ethyl-di-tert-butylphosphine, and the yield was 96%. The e. e. % was 99.3%. $^{31}$P NMR (400 MHz, CDCl$_3$), δ: −26.0 (d, J=50.8 Hz), 49.8 (d, J=50.7 Hz); $^1$H NMR (400 MHz, CDCl$_3$), δ: 7.65-7.61 (m, 2H, Ph), 7.35-7.14 (m, 8H, Ph), 4.37-4.22 (m, 3H, Fc-H), 3.84(s, 5H, Fc-H), 3.43 (m, 1H), 1.84(dd, J=7.2 Hz, J=3.0 Hz, 3H), 1.14(d, J=10.2 Hz, 9H), 0.98 (d, J=10.2 Hz, 9H). HRMS: Calcd for C$_{32}$H$_{40}$FeP$_2$ 542.1955, Found 542.1192. Measured value (calculated value) of element analysis/%: C 70.82 (70.85), H 7.41 (7.43).

EXAMPLE 2

(1) Synthesis of (R)-1-ferrocenylethyl-dicyclohexylphosphine

Under argon atmosphere, vinylferrocene (1 mol, 212 g), (R)-3,3'-bis(3,5-dimethylphenyl)-1,1'-binaphthyl-2,2'-diyl-hydrogenphosphate (0.1 mol, 55 g), and 1 L of toluene were added to a first drying reactor in that order. Dicyclohexylphosphine (1 mol, 198 g) was added to the first drying reactor, and allow to react for 10 hrs at 100° C. The first drying reactor was cooled. Water was added dropwise to the first drying reactor. Liquid separation was performed, and the organic layer was dried over anhydrous magnesium sulfate, then filtrated, and distilled at reduced pressure to remove solvent and yield yellow solid. The yellow solid was recrystallized in dichloromethane and methyl alcohol to yield 394 g of (R)-1-ferrocenylethyl-dicyclohexylphosphine, and the yield was 96%. The e. e. % was 99.4%. $^{31}$P NMR (400 MHz, CDCl$_3$), δ: 14.6; $^1$H NMR (400 MHz, CDCl$_3$), δ: 4.37-4.12 (m, 4H, Fc-H), 3.91(m, 5H, Fc-H), 3.46 (m, 1H), 1.92-1.03(m, 25H); HRMS: Calcd for C$_{24}$H$_{35}$FeP 410.1826, Found 410.1823; measured value (calculated value) of element analysis/%: C 70.24 (70.25), H 8.58 (8.60).

(2) Synthesis of (R)-(−)-1-((S)-2-diphosphino ferrocene)-ethyl-dicyclohexylphosphine Under argon atmosphere, (R)-1-ferrocenylethyl-dicyclohexylphosphine (0.9 mol, 369 g), and 1 L of ether were added to a second drying reactor. 1 mol/L of hexane solution (1.35 mol, 1.35 L) containing diethylzinc was added to the second drying reactor and allow to react for 1 hr at 30° C. Diphenylchlorophosphine (1.7 mol, 376 g) was added dropwise to reaction mixture, and the reaction mixture was heated and refluxed for 3 hrs. Water was added to quench the reaction mixture. Liquid separation of the reaction mixture was performed, and the organic layer was dried over anhydrous magnesium sulfate, then filtrated, and distilled at reduced pressure to remove solvent and yield yellow solid. The yellow solid was recrystallized in dichloromethane and methyl alcohol to yield 518 g of (R)-(−)-1-((S)-2-diphosphino ferrocene)-ethyl-dicyclohexylphosphine, and the yield was 97%. The e. e. % was 99.2%. $^{31}$P NMR (400 MHz, CDCl$_3$), δ: −24.6 (d, J=30.2 Hz), 15.1 (d, J=30.3 Hz); $^1$H NMR (400 MHz, CDCl$_3$), δ: 7.62-7.56 (m, 2H, Ph),7.34-7.11 (m, 8H, Ph), 4.38-4.13 (m, 3H, Fc-H), 3.86(m, 5H, Fc-H), 3.42 (m, 1H), 1.93-1.01(m, 25H). HRMS: Calcd for C$_{36}$H$_{44}$FeP$_2$ 594.2268, Found 594.2265. Measured value (calculated value) of element analysis/%: C 72.71 (72.73), H 7.45 (7.46).

EXAMPLE 3

(1) Synthesis of
(R)-1-ferrocenylethyl-diphenylphosphine

Under argon atmosphere, vinylferrocene (1 mol, 212 g), (R)-3,3'-bis(3,5-dimethylphenyl)-1,1'-binaphthyl-2,2'-diyl-hydrogenphosphate (0.01 mol, 5.6 g), and 1 L of toluene were added to a first drying reactor in that order. Diphenylphosphine (1 mol, 186 g) was added to the first drying reactor, and allow to react for 12 hrs at 60° C. The first drying reactor was cooled. Water was added dropwise to the first drying reactor. Liquid separation was performed, and the organic layer was dried over anhydrous magnesium sulfate, then filtrated, and distilled at reduced pressure to remove solvent and yield yellow solid. The yellow solid was recrystallized in dichloromethane and methyl alcohol to yield 386 g of (R)-1-ferrocenylethyl-diphenylphosphine, and the yield was 97%. The e. e. % was 99.2%. $^{31}$P NMR (400 MHz, CDCl$_3$), δ: 4.6; $^1$H NMR (400 MHz, CDCl$_3$), δ: 7.23-7.82(m, 10H), 4.35-4.14 (m, 4H, Fc-H), 3.93 (m, 5H, Fc-H), 3.44 (m, 1H), 1.58 (dd, J=7.2 Hz, J=3.0 Hz, 3H).

(2) Synthesis of (R)-(−)-1-((S)-2-diphosphino ferrocene)-ethyl-diphenylphosphine Under argon atmosphere, (R)-1-ferrocenylethyl-diphenylphosphine (0.9 mol, 358 g), and 1 L of ether were added to a second drying reactor. 1 mol/L of hexane solution (0.9 mol, 0.9 L) containing diethylzinc was added to the second drying reactor and allow to react for 3 hrs at 0° C. Diphenylchlorophosphine (0.9 mol, 199 g) was added dropwise to reaction mixture, and the reaction mixture was heated and refluxed for 2 hrs. Water was added to quench the reaction mixture. Liquid separation of the reaction mixture was performed, and the organic layer was dried over anhydrous magnesium sulfate, then filtrated, and distilled at reduced pressure to remove solvent and yield yellow solid. The yellow solid was recrystallized in dichloromethane and methyl alcohol to yield 558 g of (R)-(−)-1-((S)-2-diphosphino ferrocene)-ethyl-diphenylphosphine, and the yield was 96%. The e. e. % was 99.3%. $^{31}$P NMR (400 MHz, CDCl$_3$), δ: −25.6 (d, J=20.8 Hz), 5.8 (d, J=20.8 Hz); $^1$H NMR (400 MHz, CDCl$_3$), δ: 7.21-7.83(m, 20H), 4.36-4.15 (m, 3H, Fc-H), 3.93 (m, 5H, Fc-H), 3.45 (m, 1H), 1.59 (dd, J=7.2 Hz, J=3.0 Hz, 3H).

EXAMPLE 4

(1) Synthesis of (R)-1-ferrocenylethyl-bis(3,5-dimethylphenyl)-phosphine

Under argon atmosphere, vinylferrocene (1 mol, 212 g), (R)-3,3'-bis(3,5-dimethylphenyl)-1,1'-binaphthyl-2,2'-diyl hydrogenphosphate (0.01 mol, 5.6 g), and 1 L of toluene were added to a first drying reactor in that order. Bis(3,5-dimethylphenyl)-phosphine (1 mol, 242 g) was added to the first drying reactor, and allow to react for 12 hrs at 60° C. The first drying reactor was cooled. Water was added dropwise to the first drying reactor. Liquid separation was performed, and the organic layer was dried over anhydrous magnesium sulfate, then filtrated, and distilled at reduced pressure to remove solvent and yield yellow solid. The yellow solid was recrystallized in dichloromethane and methyl alcohol to yield 436 g of (R)-1-ferrocenylethyl-bis (3,5-dimethylphenyl)-phosphine, and the yield was 96%. The e. e. % was 99.2%. $^{31}$P NMR (400 MHz, CDCl$_3$), δ: 4.7; $^1$H NMR (400 MHz, CDCl$_3$), δ: 7.25-7.80(m, 6H), 4.35-4.14 (m, 4H, Fc-H), 3.91 (m, 5H, Fc-H), 3.44 (m, 1H), 2.16 (m, 6H), 2.25 (m, 6H), 1.59 (dd, J=7.2 Hz, J=3.0 Hz, 3H).

(2) Synthesis of (R)-(−)-1-((S)-2-diphosphino ferrocene)-ethyl-bis(3,5-dimethylphenyl)-phosphine Under argon atmosphere, (R)-1-ferrocenylethyl-bis(3,5-dimethylphenyl)-phosphine (0.9 mol, 409 g), and 1 L of ether were added to a second drying reactor. 1 mol/L of hexane solution (0.9 mol, 0.9 L) containing diethylzinc was added to the second drying reactor and allow to react for 1 hr at 20° C. Diphenylchlorophosphine (0.9 mol, 199 g) was added dropwise to reaction mixture, and the reaction mixture was heated and refluxed for 2 hrs. Water was added to quench the reaction mixture. Liquid separation of the reaction mixture was performed, and the organic layer was dried over anhydrous magnesium sulfate, then filtrated, and distilled at reduced pressure to remove solvent and yield yellow solid. The yellow solid was recrystallized in dichloromethane and methyl alcohol to yield 612 g of (R)-(−)-1-((S)-2-diphosphino ferrocene)-ethyl-bis(3,5-dimethylphenyl)-phosphine, and the yield was 96%. The e. e. % was 99.3%.$^{31}$P NMR (400 MHz, CDCl$_3$), δ: −25.7 (d, J=20.5 Hz), 6.0 (d, J=20.5 Hz); $^1$H NMR (400 MHz, CDCl$_3$), δ: 7.18-7.85(m, 16H), 4.38-4.13 (m, 3H, Fc-H), 3.90 (m, 5H, Fc-H), 3.45 (m, 1H), 2.15 (m, 6H), 2.24 (m, 6H), 1.61 (dd, J=7.2 Hz, J=3.0 Hz, 3H).

EXAMPLE 5

(1) Synthesis of
(R)-1-ferrocenylethyl-diphenylphosphine

Under argon atmosphere, vinylferrocene (1 mol, 212 g), (R)-3,3'-bis(3,5-dimethylphenyl)-1,1'-binaphthyl-2,2'-diyl-hydrogenphosphate (0.05 mol, 28 g), and 1 L of toluene were added to a first drying reactor in that order. Diphenylphosphine (1.3 mol, 242 g) was added to the first drying reactor, and allow to react for 12 hrs at 60° C. The first drying reactor was cooled. Water was added dropwise to the first drying reactor. Liquid separation was performed, and the organic layer was dried over anhydrous magnesium sulfate, then filtrated, and distilled at reduced pressure to remove solvent and yield yellow solid. The yellow solid was recrystallized in dichloromethane and methyl alcohol to yield 386 g of (R)-1-ferrocenylethyl-diphenylphosphine, and the yield was 97%. The e. e. % was 99.1%.

(2) Synthesis of (R)-(−)-1-((S)-2-(di-tert-butylphosphine) ferrocene)-ethyl-diphenylphosphine Under argon atmosphere, (R)-1-ferrocenylethyl-diphenylphosphine (0.9 mol, 358 g), and 1 L of ether were added to a second drying reactor. 1 mol/L of hexane solution (0.9 mol, 0.9 L) containing diethylzinc was added to the second drying reactor and allow to react for 3 hrs at 0° C. Di-tert-butylchlorophosphine (1.1 mol, 198 g) was added dropwise to reaction mixture, and the reaction mixture was heated and refluxed for 2 hrs. Water was added to quench the reaction mixture. Liquid separation of the reaction mixture was performed, and the organic layer was dried over anhydrous magnesium sulfate, then filtrated, and distilled at reduced pressure to remove solvent and yield yellow solid. The yellow solid was recrystallized in dichloromethane and methyl alcohol to yield 520 g of (R)-(−)-1-((S)-2-(di-tert-butylphosphine) ferrocene)-ethyl-diphenylphosphine, and the yield was 96%. The e. e. % was 99.3%. $^{31}$P NMR (400 MHz, CDCl$_3$), δ: −26.7 (d, J=3.8 Hz), 14.4 (d, J=3.8 Hz); $^1$H NMR (400 MHz, CDCl$_3$), δ: 7.23-7.78(m, 10H), 4.37-4.14 (m, 3H, Fc-H), 3.90 (m, 5H, Fc-H), 3.45 (m, 1H), 1.59 (m, 3H), 1.58(d, J=11.3 Hz, 9H), 1.05(d, J=11.3 Hz, 9H).

EXAMPLE 6

(1) Synthesis of (R)-1-ferrocenylethyl-di-tert-butylphosphine

Under argon atmosphere, vinylferrocene (1 mol, 212 g), (R)-3,3'-bis(3,5-dimethylphenyl)-1,1'-binaphthyl-2,2'-diyl-hydrogenphosphate (0.05 mol, 28 g), and 1 L of toluene were added to a first drying reactor in that order. Di-tert-butylphosphine (1.1 mol, 162 g) was added to the first drying reactor, and allow to react for 12 hrs at 80° C. The first drying reactor was cooled. Water was added dropwise to the first drying reactor. Liquid separation was performed, and the organic layer was dried over anhydrous magnesium sulfate, then filtrated, and distilled at reduced pressure to remove solvent and yield yellow solid. The yellow solid was recrystallized in dichloromethane and methyl alcohol to yield 343 g of (R)-1-ferrocenylethyl-di-tert-butylphosphine, and the yield was 96%. The e. e. % was 99.4%.

(2) Synthesis of (R)-(−)-1-((S)-2-dicyclohexylphosphine ferrocene)-ethyl-di-tert-butylphosphine Under argon atmosphere, (R)-1-ferrocenylethyl-di-tert-butylphosphine (0.9 mol, 321 g), and 1 L of ether were added to a second drying reactor. 1 mol/L of hexane solution (0.9 mol, 0.9 L) containing diethylzinc was added to the second drying reactor and allow to react for 3 hrs at 0° C. Dicyclohexylchlorophosphine (1.0 mol, 255 g) was added dropwise to reaction mixture, and the reaction mixture was heated and refluxed for 2 hrs. Water was added to quench the reaction mixture. Liquid separation of the reaction mixture was performed, and the organic layer was dried over anhydrous magnesium sulfate, then filtrated, and distilled at reduced pressure to remove solvent and yield yellow solid. The yellow solid was recrystallized in dichloromethane and methyl alcohol to yield 532 g of (R)-(−)-1-((S)-2-dicyclohexylphosphine ferrocene)-ethyl-di-tert-butylphosphine, and the yield was 96%. The e. e. % was 99.2%. $^{31}$P NMR (400 MHz, CDCl$_3$), δ: −15.4 (d, J=16.6 Hz), 47.5 (d, J=16.6 Hz); $^1$H NMR (400 MHz, CDCl$_3$), δ: 4.44-4.22 (m, 3H, Fc-H), 4.09(s, 5H, Fc-H), 3.38 (m, 1H), 2.32-2.26(m, 2H), 2.14-2.06 (m, 2H), 1.87-1.08(m, 39H).

Unless otherwise indicated, the numerical ranges involved in the invention include the end values. While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A method for synthesizing (R)-(−)-1-((S)-2-diphosphino ferrocene)-ethyl-diphosphine, the method comprising:
   1) adding vinylferrocene, a chiral catalyst, and toluene as a solvent to a first drying reactor under inert gas protection; adding a phosphorus-hydrogen compound to the first drying reactor and allowing reactants in the first drying reactor to react for between 10 and 12 hrs at a temperature of between 60 and 100° C.; cooling the first drying reactor; adding water dropwise to the first drying reactor; extracting, drying, and recrystallizing a product to yield (R)-1-ferrocenylethyl-diphosphine; and
   2) adding the (R)-1-ferrocenylethyl-diphosphine and ether as a solvent to a second drying reactor under inert gas protection; adding a hexane solution comprising diethylzinc to the second drying reactor and allowing reactants in the second drying reactor to react for between 1 and 3 hr(s) at a temperature of between 0 and 30° C.; adding a phosphorus-chlorine compound dropwise to the second drying reactor, and heating and refluxing the second drying reactor for between 2 to 3 hrs; adding water to quench a reaction mixture in the second drying reactor; and extracting, drying, and recrystallizing the reaction mixture to yield (R)-(−)-1-((S)-2-diphosphino ferrocene)-ethyl-diphosphine;

wherein the phosphorus-hydrogen compound is di-tert-butylphosphine, dicyclohexylphosphine, diphenylphosphine, or bis(3,5-dimethylphenyl)-phosphine;

the phosphorus-chlorine compound is di-tert-butylchlorophosphine, dicyclohexylchlorophosphine, or diphenylchlorophosphine;

the chiral catalyst is (R)-3,3'-bis(3,5-dimethylphenyl)-1,1'-binaphthyl-2,2'-diyl hydrogenphosphate, and a structural formula of the chiral catalyst is:

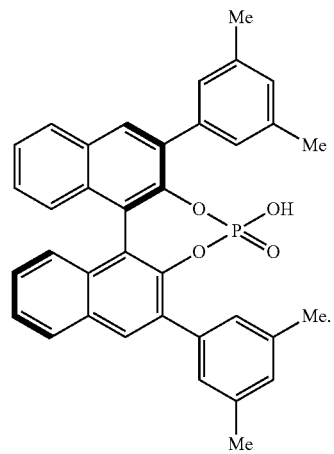

2. The method of claim 1, wherein a molar ratio of the vinylferrocene to the chiral catalyst to the phosphorus-hydrogen compound is 1: 0.01-0.1:1-1.5.

3. The method of claim 1, wherein a molar ratio of the (R)-1-ferrocenylethyl-diphosphine to the diethylzinc is 1:1-1.5; and a molar ratio of the diethylzinc to the phosphorus-chlorine compound is 1:1-1.3.

* * * * *